(12) United States Patent
Mandimutsira et al.

(10) Patent No.: US 8,124,555 B2
(45) Date of Patent: Feb. 28, 2012

(54) PROCESS FOR MAKING TITANIUM-MWW ZEOLITE

(75) Inventors: Beaven S. Mandimutsira, Wynnewood, PA (US); Jay F. Miller, Chester Springs, PA (US)

(73) Assignee: Lyondell Chemical Technology L.P., Houston, TX (US)

( * ) Notice: Subject to any disclaimer, the term of this patent is extended or adjusted under 35 U.S.C. 154(b) by 0 days.

(21) Appl. No.: 12/658,029

(22) Filed: Feb. 1, 2010

(65) Prior Publication Data

US 2011/0190517 A1    Aug. 4, 2011

(51) Int. Cl.
*B01J 29/06* (2006.01)
*B01J 29/89* (2006.01)
*B01J 21/00* (2006.01)
*C07D 301/12* (2006.01)
*C07D 301/06* (2006.01)

(52) U.S. Cl. .......... 502/64; 502/107; 502/242; 549/531; 549/533

(58) Field of Classification Search .............. 502/64, 502/107, 242; 549/531, 533
See application file for complete search history.

(56) References Cited

U.S. PATENT DOCUMENTS

| 3,351,635 | A | 11/1967 | Kollar |
| 4,367,342 | A | 1/1983 | Wulff et al. |
| 4,833,260 | A | 5/1989 | Neri et al. |
| 6,759,540 | B2 | 7/2004 | Oguchi et al. |
| 7,501,532 | B1 * | 3/2009 | Le-Khac ............ 549/531 |
| 7,863,467 | B2 * | 1/2011 | Ishino et al. ......... 549/533 |

* cited by examiner

FOREIGN PATENT DOCUMENTS

JP    4-352771    5/1991

OTHER PUBLICATIONS

Wu et al., "A Novel Titanosilicate with MWW Structure. I. Hydrothermal Synthesis, Elimination of Extraframework Titanium, and Characterizations," *Journal of Physical Chemistry B*, 105, (2001), p. 2897-2905.

*Primary Examiner* — Taylor Victor Oh

(57) ABSTRACT

Titanium-MWW zeolite is prepared by heating a gel formed from a titanium compound, a silicon source, a boron source, an MWW-templating agent, and water at a temperature in the range of 35° C. to 75° C. for a period of 8 to 30 hours to form a pre-crystallized gel, and heating the pre-crystallized gel to a temperature in the range of 160° C. to 190° C. for a period of 5 or more days to form the titanium-MWW zeolite. The zeolite, after it is contacted with an acid, is useful in olefin epoxidation with hydrogen peroxide.

19 Claims, No Drawings

PROCESS FOR MAKING TITANIUM-MWW ZEOLITE

FIELD OF THE INVENTION

This invention relates to a process for producing a titanium-MWW zeolite and its use in olefin epoxidation with hydrogen peroxide.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology, see, e.g., U.S. Pat. Nos. 3,351,635 and 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and organic hydroperoxides, another oxidizing agent useful for the preparation of epoxides is hydrogen peroxide. U.S. Pat. No. 4,833,260, for example, discloses the epoxidation of olefins with hydrogen peroxide in the presence of a titanium zeolite catalyst. Much current research is conducted in the direct epoxidation of olefins with oxygen and hydrogen. Many different direct epoxidation catalysts have been proposed. Typically, the catalyst comprises a noble metal that is supported on a titanium zeolite. For example, JP 4-352771 discloses the formation of propylene oxide from propylene, oxygen, and hydrogen using a catalyst containing a Group VIII metal such as palladium on a titanium silicalite.

One new titanium zeolite catalyst for use in olefin epoxidation reactions is titanium-MWW zeolite. Titanium-MWW zeolites are typically produced by a hydrothermal crystallization procedure, for example, as described in U.S. Pat. No. 6,759,540 and Wu et al., *J. Phys. Chem. B,* 2001, 105, p. 2897. Unfortunately, the previous processes to produce titanium-MWW are lengthy. The references teach high temperature crystallization processes, requiring prolonged heating at 130° C. for 1 day, 150° C. for 1 more day, and finally 170° C. for 5 or more days to complete the titanium-MWW synthesis.

In sum, new processes for producing titanium-MWW zeolites are needed. Particularly valuable would be processes that form high activity catalysts more efficiently.

SUMMARY OF THE INVENTION

The invention is a process for producing a titanium-MWW zeolite and its use in the epoxidation of olefins with hydrogen peroxide. The process comprises heating a gel formed from a titanium compound, a silicon source, a boron source, an MWW-templating agent, and water at a temperature in the range of 35° C. to 75° C. for a period of 8 to 30 hours to form a pre-crystallized gel; and heating the pre-crystallized gel to a temperature in the range of 160° C. to 190° C. for a period of 5 or more days to form the titanium-MWW zeolite. The zeolite, after it is contacted with an acid, is active in olefin epoxidations with hydrogen peroxide.

DETAILED DESCRIPTION OF THE INVENTION

The process of the invention is used to produce a titanium-MWW zeolite. Titanium zeolites comprise the class of zeolitic substances wherein titanium atoms are substituted for a portion of the silicon atoms in the lattice framework of a molecular sieve. Titanium-MWW zeolite is a porous molecular sieve zeolite having an MEL topology analogous to that of the MWW aluminosilicate zeolites, containing titanium atoms substituted in the framework. Such substances, and their production, are well known in the art. See for example, U.S. Pat. No. 6,759,540 and Wu et al., *J. Phys. Chem. B,* 2001, 105, p. 2897.

The titanium-MWW zeolite preferably contains no elements other than titanium, silicon, and oxygen in the lattice framework (it will also contain a significant amount of boron that can be removed by contact with an acid), although minor amounts of iron, aluminum, sodium, potassium, copper and the like may be present.

The titanium-MWW zeolite will generally have a composition corresponding to the following empirical formula $xTiO_2 \cdot (1-x)SiO_2$ where x is between 0.0001 and 0.5. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich MWW zeolites may also be desirable.

The process of the invention comprises first heating a gel formed from a titanium compound, a silicon source, a boron source, an MWW-templating agent, and water at a temperature in the range of 35 to 75° C. for a period of 8 to 30 hours to form a pre-crystallized gel. Although the process of the invention is not limited by choice of a particular titanium compound, suitable titanium compounds useful in the invention include, but are not limited to, titanium alkoxides, titanium halides, and mixtures thereof. Preferred titanium alkoxides are titanium tetraisopropoxide, titanium tetraethoxide and titanium tetrabutoxide. Titanium tetrabutoxide is especially preferred. Preferred titanium halides include titanium trichloride and titanium tetrachloride.

Suitable silicon sources include, but are not limited to, colloidal silica, fumed silica, silicon alkoxides, and mixtures thereof. Preferred silicon alkoxides are tetraethylorthosilicate, tetramethylorthosilicate, and the like. Fumed silica is especially preferred.

The MWW-templating agent is preferably piperidine, hexamethyleneimine, or adamantyl ammonium hydroxide. Piperidine and hexamethyleneimine are particularly preferred, and piperidine is most preferred.

Suitable boron sources include boric acid, boron halides, boron hydrides, borate esters, and metal borates, such as alkali metal borates. Boric acid is particularly preferred.

The gel also comprises water. In addition to water, other solvents such as alcohols may also be present. Alcohols such as isopropyl, ethyl and methyl alcohol are preferred, and isopropyl alcohol is especially preferred.

Generally, the gel has molar ratios of additives (as defined in terms of moles of MWW-templating agent, moles of $SiO_2$ and moles of $TiO_2$) which comprise the following molar ratios: $TiO_2:SiO_2=0.5-5:100$; and MWW-templating agent: $SiO_2=10-50:100$. The water:$SiO_2$ molar ratio is typically from about 1000-5000:100 and, if used, the solvent:$SiO_2$ molar ratio may be in the range of 0-500:100.

The gel can be suitably prepared by mixing the desired sources of titanium, boron, and silicon with MWW-templating agent and water in any particular order. Preferably, a mixture containing the titanium compound, the silicon source, the MWW-templating agent, and water is mixed with a second mixture containing the boron source, the silicon source, the MWW-templating agent, and water to produce the gel. Preferably, the gel mixture has a pH of about 9 to about 13. The basicity of the mixture is controlled by the amount of MWW-templating agent which is added, although other basic compounds such as ammonium hydroxide or tetramethyl ammonium hydroxide can also be added to the gel mixture.

Synthesis of the titanium-MWW zeolite is carried out by a hydrothermal crystallization. The gel is heated at a temperature in the range of 35° C. to 75° C. for a period of 8 to 30 hours to form a pre-crystallized gel. Preferably, the gel mixture is heated at a temperature of 40° C. to 70° C. for a period of 10 hours to 24 hours, more preferably from 45° C. to 70° C., and most preferably from 45° C. to 65° C. The heating time preferably does not include the time required to reach the desired temperature, but only the time that the gel is heated at the desired temperature. Preferably, the The gel is preferably heated in a sealed vessel under autogenous pressure to produce the pre-crystallized gel.

After the lower temperature pre-crystallization, the pre-crystallized gel is heated to a temperature in the range of 160° C. to 190° C. for a period of 5 or more days to form titanium-MWW zeolite. Preferably, the pre-crystallized gel is heated at a temperature of 165° C. to 185° C. for a period of 5 to 8 days, and more preferably for a period of 5 to 7 days. The pre-crystallized gel is preferably heated in a sealed vessel under autogenous pressure.

Preferably, the pre-crystallized gel is heated at a temperature in the range of 120° C. to 155° C. for a period of 8 to 30 hours prior to heating at a temperature in the range of 160° C. to 190° C. More preferably, the pre-crystallized gel is heated at a temperature in the range of 130° C. to 155° C. for a period of 8 to 24 hours prior to heating at a temperature in the range of 160° C. to 190° C.

Following crystallization, the titanium-MWW zeolite is typically recovered. Suitable zeolite recovery methods include filtration and washing (preferably with deionized water until the pH of the filtrate is approximately 10), rotary evaporation, centrifugation, and the like. The zeolite may be dried at a temperature greater than 20° C., preferably from 50° C. to 100° C.

In order to produce an active catalyst for epoxidation, the titanium-MWW zeolite is contacted with an acid to remove octahedral, inactive, extra-framework titanium as well as structural boron which acts as Bronsted acid sites. Preferably, the acid is nitric acid or sulfuric acid. Preferably, the acid is an acid solution used in a concentration of 0.5 M to 5 M, and is preferably used at a loading of 10-30 mL of the acid solution for every gram of titanium-MWW zeolite. Preferably, the acid contact occurs at elevated temperatures, more preferably under reflux conditions. In addition to removing octahedral, inactive, extra-framework titanium, the acid wash typically removes some of the MWW-templating agent contained in the zeolite pores and initiates the conversion of the material from its 2-dimensional layer form to the extended 3-dimensional form. Following the acid contact, the titanium-MWW zeolite is preferably washed with water, more preferably it is washed with water until the filtrate has a pH of 4 or greater.

Preferably, the titanium-MWW zeolite is calcined to remove any remaining MWW-templating agent at temperatures from 400° C. to 800° C., more preferably from 530° C. to 600° C. The calcination typically is preferably conducted in an oxygen-containing atmosphere, such as air or a mixture of oxygen and an inert gas such as nitrogen. The catalyst may also be calcined (pyrolyzed) in the presence of an inert gas such as nitrogen, and then optionally, calcined in an oxygen-containing atmosphere.

The epoxidation process of the invention comprises contacting an olefin and hydrogen peroxide in the presence of the acid-contacted titanium-MWW zeolite. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may contain only carbon and hydrogen atoms, or may contain functional groups such as halide, carboxyl, hydroxyl, ether, carbonyl, cyano, or nitro groups, or the like. The process of the invention is especially useful for converting propylene to propylene oxide.

The hydrogen peroxide may be generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical pre-formed hydrogen peroxide concentrations range from 0.1 to 90 weight percent hydrogen peroxide in water, preferably 1 to 10 weight percent.

The amount of pre-formed hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred. Thus, in one preferred embodiment of the invention, the epoxidation of olefin with oxygen and hydrogen is carried out in the presence of a noble metal catalyst and the titanium-MWW zeolite produced by the methods described above.

While any noble metal catalyst can be utilized (i.e., gold, silver, platinum, palladium, iridium, ruthenium, osmium metal catalysts), either alone or in combination, palladium, platinum and gold metal catalysts are particularly desirable. Suitable noble metal catalysts include high surface area noble metals, noble metal alloys, and supported noble metal catalysts. Examples of suitable noble metal catalysts include high surface area palladium and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 m²/g, more preferably from about 50 to about 500 m²/g, and most preferably from about 100 to about 400 m²/g. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 µm, more preferably from about 1 to about 200 µm, and most preferably from about 10 to about 100 µm. The average pore diameter is typically in the range of about 10 to about 1000 Å, preferably about 20 to about 500 Å, and most preferably about 50 to about 350 Å.

The supported noble metal catalyst contains a noble metal (i.e., gold, silver, platinum, palladium, iridium, ruthenium, osmium). Palladium, platinum, gold, and mixtures thereof are particularly desirable. Typically, the amount of noble metal present in the supported catalyst will be in the range of from 0.001 to 20 weight percent, preferably 0.005 to 10 weight percent, and particularly 0.01 to 5 weight percent. The manner in which the noble metal is incorporated into the supported catalyst is not considered to be particularly critical. For example, the noble metal may be supported by impregnation, adsorption, precipitation, or the like. Alternatively, the noble metal can be incorporated by ion-exchange with, for example, tetraamine palladium dichloride.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate), amine, and ammonium complexes of noble metals.

In another preferred embodiment of the invention, the epoxidation of olefin, hydrogen and oxygen is carried out in the presence of a noble metal-containing titanium-MWW which comprises a noble metal and the titanium-MWW zeolite of the invention. In this embodiment, the noble metal is incorporated into the titanium-MWW zeolite by the methods described above.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

Preferably, epoxidation is carried out in the liquid (or supercritical or subcritical) phase. It is advantageous to work at a pressure of 1-200 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, nitriles such as acetonitrile, liquid $CO_2$ (in the supercritical or subcritical state), and water. Preferable solvents include liquid $CO_2$, nitriles, alcohols, ketones, water, and mixtures thereof. Preferred nitriles include acetonitrile and other nitriles with appreciable water solubility. Preferred alcohols include lower aliphatic $C_1$-$C_4$ alcohols such as methanol, ethanol, isopropanol, and tert-butanol, or mixtures thereof. Fluorinated alcohols can be used. Most preferably, the solvent is methanol, ethanol, isopropanol, and tert-butanol, water, or mixtures thereof. It is particularly preferable to use mixtures of the cited alcohols with water.

If epoxidation is carried out in the liquid (or supercritical or subcritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may preferably range from 3 to 12, more preferably from 4 to 10 and most preferably from 5 to 9. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. Buffers may preferably contain a combination of more than one suitable salt. Typically, the concentration of buffer in the solvent is from about 0.0001 M to about 1 M, preferably from about 0.0005 M to about 0.3 M. The buffer useful in this invention may also include the addition of ammonia gas or ammonium hydroxide to the reaction system. For instance, one may use a pH=12-14 solution of ammonium hydroxide to balance the pH of the reaction system. More preferred buffers include alkali metal phosphate, ammonium phosphate, and ammonium hydroxide buffers.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0-150° C., more preferably, 20-120° C. Reaction or residence times of from about 1 minute to 48 hours, more preferably 1 minute to 8 hours will typically be appropriate. It is advantageous to work at a pressure of 1 to 200 atmospheres, although the is reaction can also be performed at atmospheric pressure.

The following examples merely illustrate the invention. Those skilled in the art will recognize many variations that are within the spirit of the invention and scope of the claims.

Example 1

Preparation of Ti-MWW Catalyst

The gel is prepared following the procedure outlined in *J. Phys. Chem. B*, 2001, 105, p. 2897. Piperidine (876 g) is dissolved in deionized water (2259 g), stirred thoroughly for 10 minutes, and the solution is split into 2 equal parts. To the first part of the piperidine solution, tetrabutyl orthotitanate (TBOT; 57 g used when Si:Ti ratio is 39; 73.5 g used when Si:Ti ratio is 29; and 66 g used when Si:Ti ratio is 34) is added under air and the mixture stirred until the TBOT is dissolved to give a colorless solution. Fumed silica (198 g) is then gradually added to this solution with vigorous stirring, and then stirred for a further 1.5 hours to produce a titanium-containing gel. To the second part of the piperidine solution, boric acid (528 g) is slowly added under vigorous stirring until dissolved and then fumed silica (198 g) is gradually added with vigorous stirring, and then stirred for a further 1.5 hours to form a boric acid-containing gel. The titanium-containing gel is added to the boric acid-containing gel and stirred for an additional 1.5 hours to form a translucent gel.

The translucent gel is fed into stainless steel autoclaves without Teflon liners and the mixture heated according to the temperature protocol shown in Tables 1 and 2. The autoclave is cooled and the solid is separated from the liquid by filtration either under nitrogen pressure or under vacuum. The resulting white solid is repeatedly rinsed with deionized water until the filtrate pH is about 10, the solid is air-dried, and then further dried at 60-80° C. in a vacuum oven for about 16 hours to produce the Ti-MWW zeolite.

The Ti-MWW zeolite is treated with nitric acid (2M $HNO_3$) at reflux for 24 hours (20 mL $HNO_3$ solution for every gram of solid). The solid product is filtered, washed with water until filtrate pH is greater than 4, and is then dried in a vacuum oven at 60-80° C. for 16 hours. The solid is then calcined under air at 600° C. for 6 hours to form the Ti-MWW catalyst. The Ti-MWW catalysts are analyzed by XRD to show the crystalline or amorphous nature of the solids (see Tables 1 and 2).

Example 2

Epoxidation of Propylene

A 100-mL Parr reactor is charged with a 70:25:5 wt. % solution of t-butanol/water/hydrogen peroxide (40 g) and Ti-MWW catalyst (0.15 g). The reactor is sealed and charged with propylene (23 to 25 g). The magnetically stirred reaction mixture is heated at 50° C. for 30 minutes at a reactor pressure about 280 psig, and is then cooled to 10° C. The liquid and gas phases are analyzed by gas chromatography. Propylene oxide and equivalents ("POE") are produced during the reaction. POE produced include propylene oxide ("PO") and the ring-opened products propylene glycol and glycol ethers. Results appear in Table 1.

The results show that 12 days total heating time is required to form active crystalline Ti-MWW when the published preparation technique (130° C., then 150° C., followed by 170° C.) is utilized. If this preparation is reduced to only 7 days total heating time, amorphous, non-active solid is produced (see Comp. Cat. 1B). Surprisingly, heating the gel at a temperature in the range of 35 to 75° C. for a period of 8 to 30 hours, followed by temperatures in the range of 160 to 190° C. for a period of 5 to 8 days resulted in crystalline titanium-MWW zeolite. Initial heating temperatures that are lower than 35° C., or higher than 75° C., fail to produce crystalline titanium-MWW zeolite, as shown in Table 2. In fact, if the gel used to produce Comparative Catalyst 1G is held at a temperature of 25° C. for up to 10 months, there is no noticeable change to the crystallinity of the resulting product.

TABLE 1

Effect of Time-Temperature on Epoxidation Activity

| Catalyst | Si/Ti molar ratio (gel) | Crystallization Time-Temperature Profile | Total Days | Nature of Product | Activity[1] |
|---|---|---|---|---|---|
| 1A* | 39 | 130° C. - 1 day<br>150° C. - 1 day<br>170° C. - 10 days | 12 | crystalline | 21 |
| 1B* | 29 | 130° C. - 1 day<br>150° C. - 1 day<br>170° C. - 5 days | 7 | mostly amorphous | — |
| 1C | 39 | 50° C. - 0.75 day<br>130° C. - 0.25 day | 8.5 | crystalline | 24.2 |
| 1D | 29 | 150° C. - 1 day<br>170° C. - 6.5 days<br>50° C. - 0.5 day<br>150° C. - 0.5 day<br>170° C. - 7 days | 8 | crystalline | 21.7 |
| 1E | 29 | 50° C. - 0.75 day<br>170° C. - 7 days | 7.75 | crystalline | 20.5 |
| 1F | 29 | 50° C. - 1 day<br>170° C. - 6 days | 7 | crystalline | 14.5 |

[1]Activity = grams POE produced/gram of catalyst per hour.
*Comparative Example

TABLE 2

Effect of Initial Heating Temperature on Ti-MWW Formation

| Catalyst | Si/Ti molar ratio (gel) | Crystallization Time-Temperature Profile | Total Days | Nature of Product |
|---|---|---|---|---|
| 1G* | 34 | 25° C. - 1 day<br>150° C. - 1 day<br>170° C. - 5 days | 7 | mostly amorphous |
| 1H | 34 | 35° C. - 0.5 day<br>150° C. - 0.5 day<br>170° C. - 7 days | 8 | crystalline |
| 1J | 34 | 50° C. - 0.75 day<br>170° C. - 7 days | 7.75 | crystalline |
| 1K | 34 | 60° C. - 0.75 day<br>170° C. - 5 days | 5.75 | crystalline |
| 1L | 34 | 70° C. - 0.75 day<br>170° C. - 6 days | 6.75 | crystalline |
| 1M* | 34 | 80° C. - 0.75 day<br>170° C. - 6 days | 6.75 | amorphous |
| 1N* | 34 | 80° C. - 0.5 day<br>150° C. - 0.5 day<br>170° C. - 7 days | 8 | crystalline + amorphous |

*Comparative Example

We claim:

1. A process for producing a crystalline titanium-MWW zeolite, which comprises:
    a) heating a gel formed from a titanium compound, a silicon source, a boron source, an MWW-templating agent, and water at a temperature in the range of 35° C. to 75° C. for a period of 8 to 30 hours to form a pre-crystallized gel; and
    b) heating the pre-crystallized gel at a temperature in the range of 160° C. to 190° C. for a period of 5 to 8 days to form the crystalline titanium-MWW zeolite.

2. The process of claim 1 wherein the titanium compound is selected from the group consisting of titanium halides, titanium alkoxides, and mixtures thereof.

3. The process of claim 2 wherein the titanium alkoxide is selected from the group consisting of titanium tetraethoxide, titanium tetraisopropoxide, titanium tetrabutoxide, and mixtures thereof.

4. The process of claim 1, wherein the silicon source is selected from the group consisting of colloidal silica, fumed silica, silicon alkoxides, and mixtures thereof.

5. The process of claim 4 wherein the silicon alkoxide is selected from the group consisting of tetraethylorthosilicate, tetramethylorthosilicate, and mixtures thereof.

6. The process of claim 1 wherein the boron source is selected from the group consisting of boric acid, boron halides, boron hydrides, borate esters, metal borates, and mixtures thereof.

7. The process of claim 1 wherein the MWW-templating agent is piperidine or hexamethyleneimine.

8. The process of claim 1 wherein the pre-crystallized gel is heated at a temperature in the range of 120° C. to 155° C. for a period of 8 to 30 hours prior to heating at a temperature in the range of 160° C. to 190° C.

9. A process comprising reacting an olefin and hydrogen peroxide in the presence of a crystalline titanium-MWW zeolite, wherein the crystalline titanium-MWW zeolite is produced by:
   a) heating a gel formed from a titanium compound, a silicon source, a boron source, an MWW-templating agent, and water at a temperature in the range of 35° C. to 75° C. for a period of 8 to 30 hours to form a pre-crystallized gel;
   b) heating the pre-crystallized gel to a temperature in the range of 160° C. to 190° C. for a period of 5 to 8 days to form the titanium-MWW zeolite; and
   c) contacting the titanium-MWW zeolite with an acid.

10. The process of claim 9 wherein the titanium compound is selected from the group consisting of titanium halides, titanium alkoxides, and mixtures thereof; the silicon source is selected from the group consisting of colloidal silica, fumed silica, silicon alkoxides, and mixtures thereof; the boron source is selected from the group consisting of boric acid, boron halides, boron hydrides, borate esters, metal borates, and mixtures thereof and the MWW-templating agent is piperidine or hexamethyleneimine.

11. The process of claim 9 wherein the acid is selected from the group consisting of nitric acid and sulfuric acid.

12. The process of claim 9 wherein the pre-crystallized gel is heated at a temperature in the range of 120° C. to 155° C. for a period of 8 to 30 hours prior to heating at a temperature in the range of 160° C. to 190° C.

13. The process of claim 9 wherein reaction of olefin and hydrogen peroxide is performed in a solvent selected form the group consisting of methanol, ethanol, isopropanol, tert-butanol, water, and mixtures thereof.

14. The process of claim 9 wherein the hydrogen peroxide is formed by the in situ reaction of hydrogen and oxygen in the presence of a noble metal catalyst.

15. The process of claim 1 wherein the crystalline titanium-MWW zeolite produced has an activity greater than 20 grams POE produced per gram of catalyst per hour.

16. A process for producing a crystalline titanium-MWW zeolite, which comprises:
   a) heating a gel formed from a titanium compound, a silicon source, a boron source, an MWW-templating agent, and water at a temperature in the range of 50° C. to 70° C. for a period of 12 to 18 hours to form a pre-crystallized gel; and
   b) heating the pre-crystallized gel at a temperature of 170° C. for a period of 5 to 7 days to form the crystalline titanium-MWW zeolite.

17. The process of claim 16 wherein the pre-crystallized gel is heated at a temperature of 150° C. for a period of 12 to 24 hours prior to heating at a temperature of 170° C.

18. The process of claim 16 wherein the pre-crystallized gel is heated at a temperature of 130° C. for a period of 8 to 12 hours followed by heating at a temperature of 150° C. for a period of 12 to 24 hours prior to heating at a temperature of 170° C.

19. The process of claim 16 wherein the crystalline titanium-MWW zeolite produced has an activity greater than 20 grams POE produced per gram of catalyst per hour.

* * * * *